United States Patent [19]
Rosenlicht

[11] Patent Number: 5,915,962
[45] Date of Patent: Jun. 29, 1999

[54] DENTAL IMPLANT AND PROSTHESIS POSITIONING

[76] Inventor: Joel L. Rosenlicht, 483 Middle Turnpike West, Manchester, Conn. 06040

[21] Appl. No.: 08/963,279

[22] Filed: Nov. 3, 1997

[51] Int. Cl.⁶ .................................................. A61C 3/00
[52] U.S. Cl. .................................................. 433/76
[58] Field of Search ................... 433/172, 173, 433/174, 175, 176, 76, 75

[56] References Cited

U.S. PATENT DOCUMENTS

| | | | |
|---|---|---|---|
| 5,133,660 | 7/1992 | Fenick | 433/76 |
| 5,183,414 | 2/1993 | Czerniawski | 433/76 |
| 5,302,122 | 4/1994 | Milne | 433/76 |
| 5,320,529 | 6/1994 | Pompa | 433/76 |
| 5,338,196 | 8/1994 | Beaty et al. | 433/173 |
| 5,556,278 | 9/1996 | Meitner | 433/75 |
| 5,636,986 | 6/1997 | Pezeshkian | 433/76 |

*Primary Examiner*—Cary E. O'Connor

[57] ABSTRACT

A kit for building a model for guiding the drilling of plural guide holes into the jaw bone of a dental patient for guiding the forming of plural adjacent cavities for the installation of plural adjacent implants and a method for guiding the drilling of such cavities are disclosed.

13 Claims, 1 Drawing Sheet

DENTAL IMPLANT AND PROSTHESIS POSITIONING

FIELD OF THE INVENTION

This invention relates to the installation of dental prosthesis systems generally and specifically to dental prosthesis systems that include an implant that is inserted into the bone for osseointegration or any other type of bone healing. Still more specifically, the present invention relates to methods and apparatus to assure that cavities are formed in the bone in proper spacing and orientation for the installation of dental implants.

BACKGROUND OF THE INVENTION

In various dental surgical procedures, jaw surgery in general and work with oral implants, it is a common practice to insert a cylindrical implant into a bore or implant cavity provided for this purpose in the jawbone of a patient.

A number of problems have been encountered in connection with the drilling of such cavities and indeed, these problems can be so severe that in some cases the use of implant techniques must be discarded since there are no anatomical conditions in which a satisfactory attachment of the implant can be guaranteed. Such cases include, for example, the lack of sufficient bone substance for an implant cavity.

However, even when there is sufficient bone substance for an implant cavity, problems have been encountered in the past in forming the implant cavity with a sufficient degree of precision, parallelism and spacing, especially where a number of implant cavities are required in a certain region of a jawbone.

Usually such bores are formed in a freehand manner in the jawbones. Of course, this can readily result in defective bores. There is a danger that the bore will be at such an inclination or position that the spongiosa or cortical bone will be excessively damaged in the transverse direction. Such damage may result in jaw resorption. The importance of the transverse dimension is that with implantation, one should ensure a thickness of about 1 mm of spongiosa between an implant and the laminar externa and interna of the respective jaw structure to ensure a sufficient blood supply around the implant and hence growth of bone tissue around the implant to anchor it. Failure to maintain precision and spacing with respect to this dimension may cause of a variety of problems. Bone grafting or other procedures may be required to assure proper orientation or positioning of the implant cavity in the bone.

When the implant is subjected to loading and when the implants are not exactly parallel to one another or to the teeth, that there is an element of transverse pressure transmission to the implant. This provides a pressure effect on one side of the implant and a tension effect on the opposite side. Both effects increase, over extended periods, the bone resorption effect and give rise to a funnel-shaped bone resorption pattern which can produce secondary infections around the implant which may lead to failure of the implant.

The prior art is replete with references to the problems inherent in providing an cavity in which a dental implant can satisfactorily be installed that will support a single tooth or, with other implants, plural teeth. As suggested, and as will be discussed in more detail, the problems inherent in drilling or cutting cavities to receive dental implants is exacerbated where plural adjacent implants must be installed.

In order to fabricate a dental prosthetic, such as a crown, inlay, bridge etc., a negative impression of a patient's mouth is taken using an impression material, and a reproduction of the impression is made as a model in the dental laboratory.

A technique has been described by Lauks in U.S. Pat. No. 4,998,881 in which a model is made from conventional impressions or negative molds of a person's teeth and gums. During the pouring and casting of the dental casting material in the negative mold, a longitudinal, tapered pin or rod is embedded in the casting material The pin or rod extends longitudinally through the base of the model beneath the teeth impressions of the model, with the pin or rod being positioned so that the longitudinal axis of the pin or rod lies in general parallel alignment with the line of the teeth in the negative mold. The pin or rod must extend along a longitudinal direction through the model that is being made such that the pin or rod extends beneath the teeth in the model. In this method, after the model has been poured and the casting material has set into a hard cast model, the model is removed from the negative mold. The longitudinal pin or rod is withdrawn and removed from the model, and the desired dies are sectioned from the model, i.e., the model is cut into the desired sections to isolate one or more teeth for which a dental prosthesis is to be made. These sections can be reassembled on the pin or rod to recreate the precise, true relationship of the teeth in the dental model prior to the cutting of the model into sections. This allows the prosthetic device being constructed to be formed to not only fit exactly the remnant of the tooth that has been prepared by the dentist but to also precisely conform with adjacent teeth of the patient's mouth. Thus, in a very, very general sense, the use of a series of individual generally cylindrical or modified cylindrical tooth emulations in the preparation of dental prostheses is known.

In the Lauks method the end of the pin or rod that extend from the dental model is made to be attached to and detached from an articulation system that allows the dental prosthetic device that is being constructed to be formed to conform and match the teeth in the opposite row of teeth for proper occlusion of the teeth as the patient bites and chews. The Lauks articulation system comprises a flex member which can be made of plastic, rubber or a spring member such as a coiled spring. The respective models are attached by way of the pin or rod of each model to opposite ends of the flex member. The models can then be moved in lateral or protrusive movements and back to centric occlusion to check proper mating of the prosthetic device with the tooth and teeth that it occludes during biting and chewing. In this step, the spacing and size of the teeth are, to some extent, taken into consideration; however, there remains the problem of providing parallel cavities in which to install the implants for supporting the prosthetic teeth.

The affixation of a tooth prosthesis to a patient is traditionally, in older procedures, achieved by basically a three stage process. In these traditional procedures, the gums are allowed to heal following extraction or loss of natural teeth. After the initial healing, surgeon cuts down through the gingiva to expose the underlying bone. The surgeon then burrs into the bone to insert a dental implant. The dental implant itself can be either press-fitted down into a hole drilled in the bone or it can be screwed down into that hole. A cover is then placed over the screw hole in the center of the anti-rotational coupling and the overlying gingiva tissue is then closed back over or around the implant. Healing is then permitted. Following this first stage healing, the surgeon cuts away the gingiva surrounding the head of the dental implant, removes the cover and then inserts a second stage healing cap onto the head of the dental implant. After a period of time, the stitches are removed and the restorative doctor and dental technician then begin the third stage: creating a prosthesis that is permanently secured to the dental implant. The healing cap is removed and a transfer impression is taken of the jaw containing the implant. To preserve the location of the opening to the dental implant when creating the stone model from the impression, an impression post is coupled to the head of the implant.

The healing cap is then reinserted into the dental implant in the patient's mouth to continue to preserve the cavity in the gingiva until either the temporary and, eventually, the permanent crown is in place. A stone model is created from the transfer impression and the stone model becomes the model from which the restorative doctor and the dental technician create the prosthesis. Ultimately, the prosthesis is installed on the implant using screws, abutments, adhesive, or other attachment or fastening means.

More modern approaches permit taking an impression earlier, e.g. at the time of extraction or the immediate installation of implants. One of the more modern approaches is described in U.S. Pat. No. 5,312,254, issued May 17, 1994 to Dr. Joel L. Rosenlicht. According to this procedure, an implant is mounted in a patient's mouth for prosthodontic restoration, in a manner requiring a minimal handling of parts, reducing patient visits, with improved results, and significantly reducing the elapsed time from the beginning to the conclusion of the prosthodontic procedure. Dr. Rosenlicht discovered that taking an impression at the first sitting of the patient, immediately following the insertion of the implants into the bone, has no significant pathological morbidity or other detrimental effects and that the location of implants, utilized in a two-stage process, remain essentially constant so that initial impressions are as accurate as impressions made following a several month healing period.

According to this more modern approach, a sterile package is provided that includes an implant having secured thereto a transfer pin which also serves as an insertion tool. The package including a carrier has a unique interior wall surface engaging the combination insertion tool/transfer pin, so that the implant may be started into the bone in a sterile manner, using the components shipped as a sterile set. According to this method, an impression is taken as soon as the carrier is removed from the combined insertion tool/transfer pin, after which the transfer pin is removed and a healing screw is inserted to the outer end of the implant in order to keep it clean for ultimate mating with an abutment which will mount the prosthesis. By taking the impression immediately—which allows the laboratory work to begin immediately for forming of the model of the mouth and the ultimate prosthesis and/or abutment structure while the initial healing takes place. This method avoids having to enter the gum tissue more than twice, since the second invasion is to remove the healing screw and mount the ultimate abutments and/or prosthesis. The procedure avoids the necessity for handling a transfer pin and concomitant screw at a second sitting, after healing has taken place. Thus, fewer steps are required, as fewer parts are handled. This significantly reduces the risk of infection as well as significantly reducing the risk of losing small parts—possibly in a patient. Another great advantage of the Rosenlicht method is that the transfer pin is always firmly and tightly secured to the implant at the factory, under ideal conditions, rather than being attached to the implant in the surgical field. A concomitant advantage is that providing a new insertion pin for each implant avoids the possibility of poor fit to the implant due to scratches in the mating surface of the transfer pin or inter-lodging debris. The invention also eliminates the use of two parts: the insertion tool and the screw used to hold the original transfer pin.

Systems for mating dental prosthetic components together are, as illustrated, well known. For example, it is now common practice to fit an abutment that forms a recess over the head of an implant. Commonly, a hex head on the implant and a mating recess on the abutment assist in vertical alignment of the prosthesis components. Ball and socket keyed components are referred to in U.S. Pat. Nos. 5,417,570 and 3,787,975 to Max Zuest. However, none of the know prior art addresses the use of articulated tooth emulations to assure spacing and alignment of implants.

The dental prosthesis art generally and the dental implant art has experienced almost explosive activity in the past decade and have become crowded art. Important progress is made, however. Sometimes, the magnitude of an advance step is not recognized because great changes is structure, materials, etc., are rarely encountered. There remain, nevertheless, very serious problems in the art, not the least of which are the problems associated with drilling holes in proper inclination to receive dental implants upon which prosthetic teeth can be mounted. Even more serious is the problem of drilling plural holes in the jaw bone at proper spacing and in proper inclination for mounting plural implants adjacent each other in the patient's jaw bone. It is to this problem that the present invention is directed.

Prior to this invention most method most procedures have involved the taking of an impression and the making mounted models so that a surgical guide stent or guide may be made. This step, making of a guide on the model, is usually non-sterile, costly, and has numerous limitations in use. It can only be used for the individual patient for whom it is made, it is difficult to alter as different anatomic problems are incurred and may be bulky.

A feature of this invention is the provision of a quick, highly accurate, and inexpensive method and means for assuring proper spacing and orientation of holes to be drilled in a patient's jaw bone to receive implants.

SUMMARY OF THE INVENTION

In one embodiment, the invention may be sold as a kit for building a model for guiding the drilling of guide holes into the jaw bone of a dental patient, thus providing guide holes for guiding the forming of adjacent cavities for the installation of adjacent implants. The kit comprises a plurality of individual elongate generally cylindrical or modified cylindrical tooth emulations. Some of these tooth emulations differ from each other as to size and shape. The individual tooth emulation, respectively, replicates as to size and lateral cross-sectional shape an individual tooth, but is truncated as necessary to provide mating keys and slots and are generally all of approximately the same length. The ends of the tooth emulation may be generally flat or concave—or any other shape if such is desired. For example, some of the tooth emulations will replicate cuspids, some will replicate molars, etc., and will be of different sizes—just as natural teeth are of differing shapes and sizes. Each tooth emulation is so constructed as to define an axis of rotation corresponding generally to the axis of the cylindrical configuration and each is so constructed as to define a pilot guide hole extending approximately along said axis of rotation. Means are associated with said tooth emulations for connecting a plurality of said tooth emulations in an articulated manner for relative movement and relative axial orientation to each other. The connecting means may be separate from and attachable to the tooth emulations or may be integrally formed as part of or into the body of the tooth emulations. In one embodiment, the means for connecting comprises a key extending from one side of each tooth emulation and a receptacle for said key formed in the opposed side of each tooth emulation. The key may be of any shape with a compatible receptacle for receiving the key. The key may, for example, be "T" shaped or "L" shaped or may be resiliently compressible; indeed, virtually any mating key and receptacle arrangement may be used.

In another embodiment, the invention is embodied in a method for fabricating guide for drilling one or more guide holes into the jaw bone of a dental patient for guiding the forming of one or more implant cavities adjacent to each other or other teeth for the installation of adjacent implants. In the course of carrying out this method, the dentist positions on the edentulous portion of the patient's jaw or on a model of the edentulous portion of the patient's jaw one or more individual elongate generally cylindrical or modified cylindrical tooth emulations as described above. The method involves selecting such tooth emulations and positioning the same on the edentulous portion of the patient's jaw, or a model thereof, to generally replicate the natural teeth that were removed from the patient. The selected tooth emulations are oriented, i.e., the respective axes of the respective tooth emulations are oriented, to cause the respective pilot guides in the respective tooth emulations to be directed toward the portion of the jaw bone into which the cavity for receiving an implant is to be formed. Once proper position, spacing and orientation are attained, the tooth emulations are luted using any conventional or convenient luting material or otherwise secured together to form a rigid model that can be placed in the patient's mouth and used for drilling through the pilot guides guide holes in the patient's jaw. While the use of luting material is simple and convenient, other means of rigidifying the stent to form a model may be used. Clamping or adhesively bonding the drill guides together, for example, may be used. The luting material may be extended to natural or existing teeth in the patient's mouth, or on replicas of the same on models, to provide even more certainty and precision in positioning, orienting and spacing the tooth emulation and, hence, the pilot guide, guide hole, implant cavity and the implant. Similarly, the drill guides may be attached by any desired mechanism to natural or existing teeth. Using the pilot guides, the dentist drills guide holes into the patients jaw and the rigid model, which defines guides for a plurality of guide holes is removed and the cavities are formed in the jaw bone following the guide holes which have been drilled.

One of the features of this invention is that by very precisely determining the position, spacing and orientation of the guide holes to be drilled, the likelihood of potential problems, some very serious involving, for example, bone grafts, etc., may be identified before the cavity is formed. Corrective procedures may then be completed in an orderly, timely manner rather than in an emergency environment. Alternatively, a change in placement, orientation or spacing of the implant my be made to obviate potential problems.

A very important feature of this invention is that any one or more of a variety of implants can be properly placed, orient and spaced to achieve a much better esthetic result. The positioning, orienting and spacing of the implant bore is very critical due to the variety of sizes, diameters and lengths of implants. The position of the implant, its spacing and orientation, which are determined by the guide hole correspond to the size and shape of the prosthesis. The present invention allows the dentist to center that bore in relationship to the size and diameter of the prosthetic tooth to be position at any particular edentulous site. The guide holes, and hence the ultimate implants, will not be equally spaced from each other or between existing teeth; rather, the guide hole will be so positioned, spaced and oriented as to permit the installation a prosthetic tooth that is a substantial replication of and esthetically replaces the extracted or lost tooth.

DESCRIPTION OF THE PREFERRED EMBODIMENTS

Figure 1:
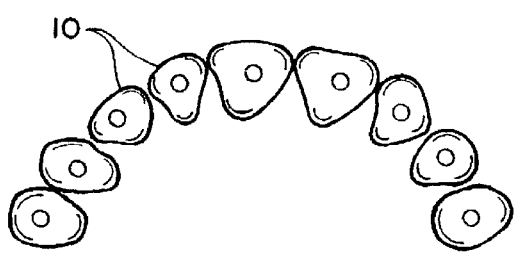
FIG. 1 is a top plan view of a plurality of generally cylindrical or modified cylindrical tooth emulations typical of such emulations that may be used in the invention.

The invention is described in reference to drawings that depict exemplary embodiments of the invention. The drawings and the description do not, however, circumscribe the invention; rather, they describe a presently preferred embodiment. With time and experience the invention and its embodiments will no doubt be refined as to materials and structural details; according, the invention is not limited by the examples given or depicted in the drawings.

The present invention may be used to install virtually any type or system of implants and prostheses and should be so construed. In the following discussion, reference will be made an "implant" which may be a screw-type implant, a cylindrical implant, a blade type implant, or any of the myriad of variants upon known implants, or any other implant which is inserted into an cavity in the maxilla or mandible of a patient. Reference will also be made to tooth prostheses. Again, virtually any kind of tooth prosthesis may be installed using the present invention.

The goal of most prosthetic dentistry is to replace original teeth with prosthetic teeth of approximately the same size and shape as the teeth being replaced and which are firmly anchored to the patient's jaw. This goal cannot be attained, in most cases, unless the implants that support the prosthetic teeth are mounted on implants that are spaced according to the size and shape of the teeth and which are generally centered laterally in the patient's mandible or maxilla. Where possible, it is desirable that the implants are oriented generally parallel to each other and centered within the prosthesis.

The present invention permits the dentist to construct a guide made up of generally cylindrical or modified cylindrical tooth emulations which can be spaced from each other and positioned relative to each other to emulate the spacing and positioning of the original teeth and which define drill guides for assuring that guide holes are drilled in the jaw bone at the proper position and orientation to permit the final cavities for receiving the implant to be positioned and oriented for maximum strength as well as to best emulate the appearance of natural teeth.

Referring first to FIG. 1, the present invention, in one embodiment at one stage of use, comprises a plurality of generally cylindrical or modified cylindrical tooth emulations generally identified at 10. As will be seen, these generally cylindrical or modified cylindrical tooth emulations are not identical but, rather, perform together as a set. It will also be seen that the generally cylindrical or modified cylindrical tooth emulations are of different size and may be of different shape. The tooth emulations have a longitudinal axis of rotation, i.e., an imaginary line around which the emulation could rotate in a symmetrical fashion, the longitudinal axis being greater that the distance perpendicular from said axis to the surface of the tooth emulation. The tooth emulations may, however, simply be cylindrical, although different shapes, as well as sizes, are usually necessary to properly replicate the size, spacing and orientation of the natural teeth. A set of emulations would generally include emulations that were, as to diameter and general shape in a lateral plane, replications of cuspids, bicuspids, molars, etc., in various sizes, i.e. major and minor diameters, such that as to size and spacing the tooth emulation would replicate any natural tooth that had been removed or lost. Some emulations may be generally round but most would not be round but would replicate the lateral cross-section of a natural tooth at or above the gum-line, being, for example, generally oval, a rounded corner generally rectangular cross-section, etc. Only that portion of the tooth above the gum-line need be replicated, of course, since it is the position and spacing above the gum line that is of interest esthetically. The emulations are described as being generally cylindrical having an axis of rotation, a more geometrically precise set of descriptors not being available. The emulations are described as elongate because the axial length of the generally cylindrical configuration is greater than the major diameter taken laterally, i.e., perpendicular to the axis of rotation. The axis of rotation is that imaginary line extending generally centrally of the emulation from one end to the other about which the emulation would rotate more or less symmetrically, the pilot guide hole generally corresponding with the axis of rotation. An emulation is considered to be generally cylindrical in the context of the present invention even if the periphery varies in distance from the axis of rotation, e.g., replicates a natural tooth shape. Generally, the ends of the cylinder would be generally flat but may desirably be slightly concave or convex and would have rounded corners, etc., so as not to damage tissue. Reference to the ends being generally flat means only that the ends of the generally cylindrical body need not replicate any particular tooth or other shape or configuration.

In one form, the invention would comprise a multiplicity of individual tooth replications that are, as will be described, capable of being articulated together as any of a large number of sets comprising different sizes, shapes, spacings and positions.

Figure 2:
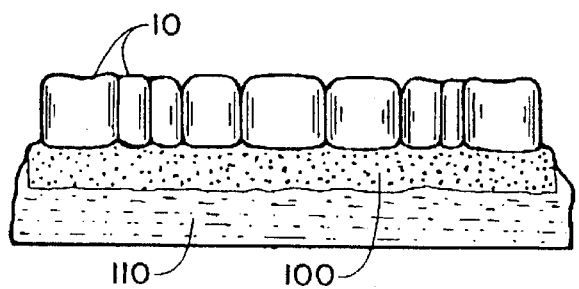
FIG. 2 is an elevational view of one side of the set of generally cylindrical or modified cylindrical tooth emulations shown in FIG. 1 positioned on a model taken of the patient's edentulous site being luted to fix the relative position of the teeth.

One such set of tooth emulations is shown in FIG. 2 positioned on a model 110 taken of the patient's edentulous site, being luted with a suitable material 100 to form a rigid guide for drilling guide holes for installing generally parallel dental implants.

Figure 3:
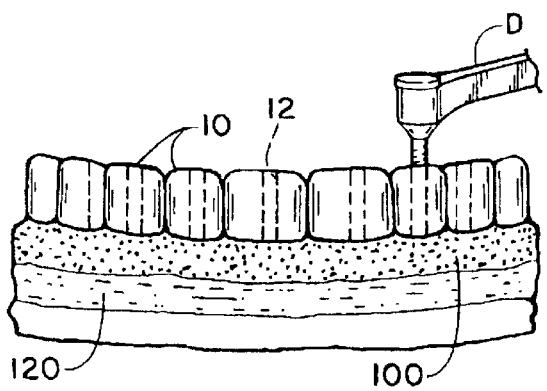
FIG. 3 is an elevational view of the other side of the set of generally cylindrical or modified cylindrical tooth emulations shown in FIG. 2 positioned in the patient's mouth over the edentulous site while a guide hole is drilled in the patient's jaw bone using the generally cylindrical or modified cylindrical tooth emulations to guide the drill as to orientation and to position the drill as to spacing.

The rigid guide shown being formed in FIG. 2 is then positioned over the edentulous site in the patient's mouth and, as shown in FIG. 3, guide holes are drilled through the pilot holes 12 formed in the individual tooth emulations.

Figure 4A:
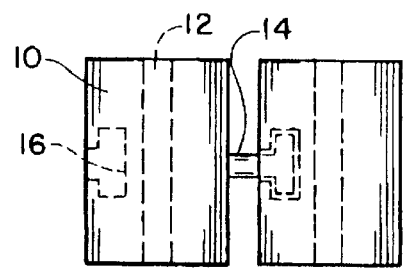
FIG. 4A depicts a pair of generally cylindrical or modified cylindrical tooth emulations connected to each other showing the keying or articulating mechanism that keeps the teeth together permitting movement thereof relative to each other and which makes possible the practice of the invention.
Figure 4B:
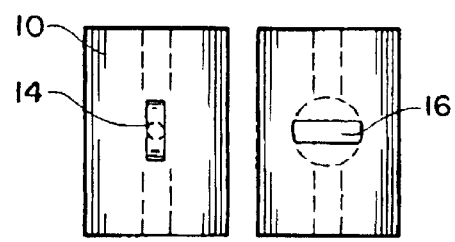
FIG. 4B depicts the pair of generally cylindrical or modified cylindrical tooth emulations shown in FIG. 4A separated from each other, showing the keying or articulating mechanism that keeps the teeth together permitting movement thereof relative to each other and which makes possible the practice of the invention.

It is critical to the proper functioning of one embodiment of the method of the invention that the individual tooth emulations be articulated together by means that will allow any of a number of sizes of teeth to be connected in any desired order and which will allow movement of the tooth emulations relative to each other. According to this method, plural guide holes are drilled adjacent each other in the jaw using adjacent tooth emulations to guide the drill. The exact method of articulation is, however, not critical and virtually any articulation connection mechanism may be used. In this regard, the terms "articulation" and "articulation mechanism" are used in an expansive sense to include mechanisms that in other contexts may not normally be regarded as articulation mechanisms. For example, one articulation mechanism is depicted in FIGS. 4A and 4B in which two tooth emulations 10, each having a pilot hole 12, are connected together by a key 14 that fits into a slot 16. The key 14 and the slot 16 each have a minor dimension and a major dimension to let the key enter the slot when the axis of one tooth emulation is perpendicular to the axis of the adjacent tooth emulation but prevents the key from removing from the slot when the axes of the tooth emulations are generally parallel. This would be one example of the many true articulation mechanisms that may be incorporated into the present invention.

Figure 5:
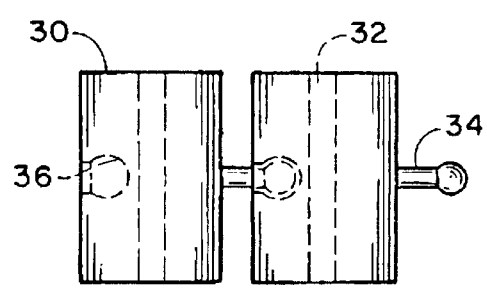
FIG. 5 depicts yet another alternative manner of articulation simply to illustrate that there are many ways of articulating the tooth emulations so that the tooth emulations can be separated and adjusted when articulated together.

Another articulation mechanism is shown in FIG. 5. This mechanism is, of course, old as a mechanism, being embodied in beads, etc. The tooth emulations 30 in FIG. 5 each define a pilot guide hole 32 and each has a projecting resilient ball 3 and defines an opposed receptacle 36 for the resilient ball.

Figure 6:
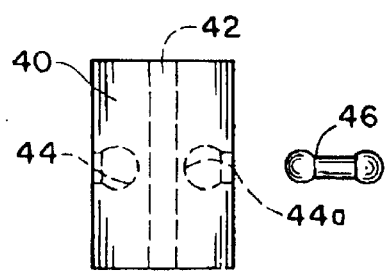
FIG. 6 depicts an alternative version of the device shown in FIG. 5 in which the connecting means is separate from the tooth emulations.

The connection system for articulating the tooth emulations shown in FIG. 6 is very similar to that shown in FIG. 6; however, each tooth emulation 40 has a pair of opposed receptacles 44 and 44a into which a separate connector 46 is inserted, one end into each tooth emulation to provide articulation.

Whatever that articulation mechanism, and nearly any will do, the individual tooth emulations can be connected together in the necessary relatively moveable relationship to permit the combined structure to be bent sufficient to emulate the curvature of the human jaw. Once articulated, the individual tooth emulations must be capable of being spaced on an imaginary curved line, that in practice would replicate the curvature of the patient's jaw, and permit the longitudinal center line of rotation, e.g. the axis in a cylinder, of the individual tooth emulations to be oriented relative to each other. This latter degree of freedom of movement is necessary to permit the pilot holes in the individual tooth emulations to be oriented to properly guide the drill into the desired central portion of the mandible or maxilla into which the implant cavity is to be formed.

As a kit, the invention may, therefor, be simply a collection of a multiplicity, e.g. five to ten and up to several dozen, individual tooth emulations and means for connecting the tooth emulations in any desired order together in an articulated, relatively moveable manner as described to define a model emulating a plurality of adjacent teeth.

As a method, the invention would be carried out after the original teeth have been extracted. Whether this would be immediately after extraction or after healing would be a choice for the dentist or surgeon. The method may be carried out directly on the patient's now edentulous jaw, or on a preliminary model of the patient's edentulous site made in the usual manner, e.g., taking an impression and from the impression fabricating a model. The first step of the invention is to connect together in an articulated manner a plurality of tooth emulations approximating the size of the natural teeth to form an articulatable model of tooth emulations. The articulatable model is positioned on the patient's edentulous site, or model thereof, and adjusted as necessary, such as by replacing respective tooth emulations to obtain the proper spacing and orienting the tooth emulations to align the pilot guide holes with the portion of the mandible or maxilla into which the implants will be affixed. Generally, the pilot guide holes 12, 32 and 42 will be generally parallel to each other; however, geometric parallelism is not required; indeed, freedom of orientation of the pilot guide holes is important in many instances to assure that the implant cavity is formed in the correct portion of the bone. Once the tooth emulations that will permit proper emulation of the natural teeth has been determined, the articulatable model is luted or otherwise rigidified to form a rigid guide for drilling guide holes into the patient's jaw bone.

Luting is a preferred form or rigidifying the drill guides because materials and techniques are well-known, but other rigidifying means and methods may be used. Examples of commercially available luting materials include Vitremer™ Luting Cement, sold by 3M Dental Products Division, St. Paul, Minn.; Advance Hybird Ionomer Cement, sold by L. D. Calk Division, Dentsply International, Milford, Del.; and Fuji Duet Reinforced Multipurpose Glass lonomer Cemet, sold by GC America, Chicago, Ill. A comparative report on such materials has been published by Dr. Mark Latta of Creighton University. Light cured composite materials are becoming popular and are commercial available from dental supply houses.

With the rigid guide positioned over the edentulous site in the patient's mouth, guide holes are drilled into the mandible or maxilla using the pilot guide holes to assure proper placement, spacing and orientation.

After the guide holes are in the patient's boney structure it is a simple matter to follow the guide hole with the size of drill required for the implant of choice. The result is that a plurality of adjacent tooth prosthesis can be installed on properly placed and properly oriented implants. The end result is a stronger set of prostheses that look more natural, all accomplished with very much less effort and time on the part of the dentist and much less risk to the patient. Truly a very new and useful result achieved by simple means by a method that has heretofore escaped the dental implant industry and the dental profession.

The material of which the tooth emulations is made is not critical, although some requirements must be met. The tooth emulations may be disposable or, as a model for drilling, kept as a unit with the patient's records. On the other hand, the tooth emulations may, as a kit, be reusable.

Material economics, of course, bears upon the manufacture of disposable tooth emulations. Such emulations could, for example, be molded of a hard polymer, in which case a metal sleeve either built into the emulation or used with the emulation may be necessary to assure that the pilot guide hole performed its necessary function. However, the guide hole could be drilled with a special drill in which the non-burred shaft fitted snugly into the pilot guide hole after a smaller burred drilling tip had passed through the pilot guide hole. Such an arrangement is shown in a general way in FIG. 7, wherein the tooth emulation 50 is shown in cross-section having a smooth pilot guide bore 52 into which the a smooth proximal shaft portion 54 is, in effect, journeled and a smaller burred cutting portion 56 extends for drilling into to the mandible or maxilla.

Reusable kits of tooth emulations would be more economical in the long term for dentists who regular do plural adjacent implant installations. Such tooth emulations could be made of titanium or stainless steel for maximum biocompatability; however, since the emulation is not in long term contact with the patient's tissue, virtually any material could be used, so long as it could be sterilized.

Figure 7:
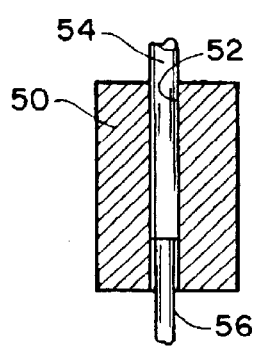
FIG. 7 depicts one technique and drill structure for drilling through the pilot guide hole of the tooth emulations.

Composite materials could, of course be used. For example, the emulation per se could be made of a metal, e.g. stainless steel, in such a way as to define a receptacle on two opposed sides and the articulation device could be made of a disposable resilient polymer that would comprise a key at each end to be inserted at the respective ends in to two adjacent emulations. Such a device is shown in FIG. 7, simply in an exemplary manner.

Traditionally, a guide hole, if used, and a cavity for an implant is drilled freehand or using a specially made guide or stent. The former approach has the inherent problems of inaccuracy and risk of improper orientation, placement, etc. The latter approach requires guide devices that are expensive, non-sterile, bulky and which do not permit precise positioning and alignment. According to the present invention, the method can be carried out by placing a single tooth emulation that replicates the diameter and generally replicates as to peripheral shape of the tooth in the space adjacent one or two natural teeth. The emulation is positioned and oriented, visually and or by way of x-ray viewing, and is secured to the adjacent tooth or teeth. This procedure can be carried out in the patient's mouth or on a model made from an impression of the appropriate portion of the patient's jawbone and teeth. In either case, a solid guide that is positioned or can be positioned at the site of the tooth to be replaced and which accurately positions and orients the guide hole for the implant cavity is available. The guide hole is drilled through the pilot guide into the jaw bone and the method proceeds the same as described above respecting plural guide holes and plural adjacent prosthesis—the prosthesis in this example being adjacent a natural tooth or previously installed implant and prosthesis.

This invention, as described, thus provides a method fabricating guide for drilling one or more guide holes into the jaw bone of a dental patient for guiding the forming of one or more implant cavities adjacent to each other or other teeth for the installation of adjacent implants. The dentist positions on the edentulous portion of the patient's jaw or on a model of the edentulous portion of the patient's jaw one or more individual elongate generally cylindrical or modified cylindrical tooth emulations as described above. Tooth emulations are selected and positioning on the edentulous portion of the patient's jaw, or on a model of that portion if desired, to generally replicate the natural teeth that were removed or lost from the patient. The selected tooth emulation is oriented, i.e., the axis of the generally cylindrical body is oriented to cause the pilot guide in the tooth emulation to be directed toward the portion of the jaw bone into which the cavity for receiving an implant is to be formed. Once proper position, spacing and orientation are attained, the tooth emulations are regidified using any conventional or convenient luting or other rigidfying means or material into a rigid model. The rigidifying material or means can be extended to adjacent existing teeth if desired for greater precision. The rigid model when positioned in the patient's mouth guides the drilling of guide holes through the pilot guides into the patient's jaw. Using the pilot guides, the dentist drills guide holes into the patients jaw and the rigid model, which defines guides for a plurality of guide holes is removed and the cavities are formed in the jaw bone following the guide holes which have been drilled. By very precisely determining the position, spacing and orientation of the guide holes to be drilled, the likelihood of potential problems is identified before the cavity is formed. Corrective procedures may then be completed in an orderly, timely manner rather than in an emergency environment or a change in placement, orientation or spacing of the implant my be made to obviate potential problems. Any one or more of a variety of implants can be properly placed, orient and spaced to achieve a much better esthetic result. The positioning, orienting and spacing of the implant bore is very critical due to the variety of sizes, diameters and lengths of implants. The position of the implant, its spacing and orientation, which are determined by the guide hole correspond to the size and shape of the prosthesis. The present invention allows the dentist to center that bore in relationship to the size and diameter of the prosthetic tooth to be position at any particular edentulous site. The guide holes, and hence the ultimate implants, will not be equally spaced from each other or between existing teeth; rather, the guide hole will be so positioned, spaced and oriented as to permit a prosthetic tooth that esthetically replaces the extracted or lost tooth.

It will be apparent to those skilled in the art that the invention can be carried out in many ways using many materials.

Industrial Application

This invention is useful in the dental implant manufacturing industry and in dentistry.

What is claimed is:

1. A kit for building a model for guiding the drilling of plural guide holes into the jaw bone of a dental patient for guiding the forming of plural adjacent cavities for the installation of plural adjacent implants comprising: a plurality of individual elongate generally cylindrical tooth emulations which generally replicate as to cross-sectional size and shape a natural tooth, some of which differ from each other as to size and shape, each of which is constructed to define an axis of rotation corresponding generally to the axis of the cylindrical configuration, each of which is so constructed as to define a pilot guide hole extending approximately along said axis of rotation, and means for connecting a plurality of said tooth emulations in an articulated manner for relative movement and relative axial orientation to each other.

2. The kit of claim 1 wherein the means for connecting comprises a key extending from one side of each tooth emulation and a receptacle for said key formed in the opposed side of each tooth emulation.

3. A method for fabricating a guide for drilling a guide hole into the at an edentulous site adjacent at least one existing tooth on the jaw bone of a dental patient from which a natural tooth has been removed or lost for guiding the forming an adjacent cavity for the installation of an adjacent implant comprising the steps of:

positioning on the edentulous site of the patient's jaw or on a model of the edentulous site of the patient's jaw adjacent at least one existing tooth an individual elongate generally cylindrical or modified cylindrical tooth emulation that generally replicates as to size and shape the natural tooth that was at such site, said emulation being so constructed as to define an axis of rotation corresponding generally to the axis of the cylindrical configuration and being so constructed as to define a pilot guide hole extending approximately along said axis of rotation;

orienting the axis of the tooth emulation to cause the pilot guide in the tooth emulation to be directed toward the portion of the jaw bone into which the cavity for receiving an implant is to be formed; and luting the tooth emulation to an adjacent tooth into a rigid model that when in the patient's mouth at the edentulous site can be used for drilling through the pilot guides a guide hole in the patient's jaw to provide orientation and positioning of a cavity for receiving an implant cavity.

4. A method for drilling a guide hole into the at an edentulous site adjacent at least one existing tooth on the jaw bone of a dental patient from which a natural tooth has been removed or lost for guiding the forming an adjacent cavity for the installation of an adjacent implant comprising the steps of:

positioning on the edentulous site of the patient's jaw or on a model of the edentulous site of the patient's jaw adjacent at least one existing tooth an individual elongate generally cylindrical or modified cylindrical tooth emulation that generally replicates as to size and shape the natural tooth that was at such site, said emulation being so constructed as to define an axis of rotation corresponding generally to the axis of the cylindrical configuration and being so constructed as to define a pilot guide hole extending approximately along said axis of rotation;

orienting the axis of the tooth emulation to cause the pilot guide in the tooth emulation to be directed toward the portion of the jaw bone into which the cavity for receiving an implant is to be formed;

securing the tooth emulation to an adjacent tooth into a rigid model that when in the patient's mouth at the edentulous site can be used for drilling through the pilot guide a guide hole in the patient's jaw to provide orientation and positioning of a cavity for receiving an implant cavity; and while the rigid model is in the patient's mouth at the edentulous site, drilling through said pilot guide a guide hole in the patient's jaw to provide orientation and positioning of a cavity for receiving an implant cavity.

5. The method of claim 4 wherein the securing step comprises extending luting material to adjacent existing teeth or replicas of such adjacent existing teeth.

6. An individual elongate tooth emulation that generally replicates as to lateral cross-sectional size and shape a natural tooth, said emulation being generally cylindrical or modified cylindrical having first and seconds ends that are generally flat or concave and so constructed as to define an axis of rotation corresponding generally to the axis of the cylindrical configuration and being so constructed as to define a pilot guide hole extending approximately along said axis of rotation and means formed in said emulation for permitting articulated connection to another such tooth emulation.

7. The tooth emulation of claim 6 further comprising means extending therefrom for permitting articulated connection to another such tooth emulation.

8. An individual elongate tooth emulation that generally replicates as to lateral cross-sectional size and shape a natural tooth, said emulation being generally cylindrical or modified cylindrical having first and seconds ends that are generally flat or concave and so constructed as to define an axis of rotation corresponding generally to the axis of the cylindrical configuration and being so constructed as to define a pilot guide hole extending approximately along said axis of rotation and means extending therefrom for permitting articulated connection to another such tooth emulation.

9. A method for fabricating guide for drilling plural guide holes into the jaw bone of a dental patient for guiding the forming of plural adjacent cavities for the installation of plural adjacent implants comprising the steps of:
- selecting and positioning on the edentulous portion of the patient's jaw or on a model of the edentulous portion of the patient's jaw to generally replicate the natural teeth that were removed or lost from the patient a plurality of individual elongate generally cylindrical tooth emulations which generally replicate as to cross-sectional size and shape a natural tooth, some of which differ from each other as to size and shape, each of which is so constructed as to define an axis of rotation corresponding generally to the axis of the cylindrical configuration, each of which is so constructed as to define a pilot guide hole extending approximately along said axis of rotation, and means associated with said tooth emulations for connecting a plurality of said tooth emulations in an articulated manner for relative movement and relative axial orientation to each other;
- orienting the axis of the respective tooth emulations to cause the respective pilot guides in the respective tooth emulations to be directed toward the portion of the jaw bone into which the cavity for receiving an implant is to be formed; and
- luting the tooth emulations into a rigid model that can be used as a guide in the patient's mouth for drilling through the pilot guides a plurality of guide holes in the patient's jaw.

10. A tooth emulation comprising a unitary body so configured as to define an overall generally cylindrical body that as to cross-sectional size and shape generally replicates that portion of a natural tooth that extends outwardly from the gum line, said body defining an imaginary axis of rotation about which the body would rotate generally symmetrically, said body having generally flat ends and defining a pilot guide hole extending approximately along said axis of rotation and means for attaching said emulation to another such tooth emulation.

11. A dental drill guide forming kit comprising a plurality of tooth emulations of different sizes and shapes, each such tooth emulation comprising a unitary body so configured as to define an overall generally cylindrical body that as to cross-sectional size and shape generally replicates that portion of a natural tooth that extends outwardly from the gum line, said body defining an imaginary axis of rotation about which the body would rotate generally symmetrically, said body having generally flat ends and defining a pilot guide hole extending approximately along said axis of rotation, said tooth emulations being constructed and configured to define means for attaching a plurality of such tooth emulations together in an articulated manner for permitting independent axial orientation of the respective tooth emulations.

12. A dental drill guide comprising a plurality of tooth emulations, each such emulation comprising a unitary body so configured as to define an overall generally cylindrical body that as to cross-sectional size and shape generally replicates that portion of a natural tooth that extends outwardly from the gum line, said body defining an imaginary axis of rotation about which the body would rotate generally symmetrically, said body having generally flat ends and defining a pilot guide hole extending approximately along said axis of rotation and means rigidly securing said tooth emulations together adjacent each other.

13. The dental drill guide of claim 12 wherein the securing means comprises solidified dental luting material.

* * * * *